US007824926B1

(12) United States Patent
Porter et al.

(10) Patent No.: US 7,824,926 B1
(45) Date of Patent: *Nov. 2, 2010

(54) RAMAN-ACTIVE REAGENTS AND THE USE THEREOF

(75) Inventors: Marc D. Porter, Ames, IA (US); Jing Ni, San Jose, CA (US); Robert J. Lipert, Ames, IA (US); G. Brent Dawson, San Jose, CA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1694 days.

This patent is subject to a terminal disclaimer.

(21) Appl. No.: 09/961,628

(22) Filed: Sep. 24, 2001

Related U.S. Application Data

(60) Provisional application No. 60/234,608, filed on Sep. 22, 2000.

(51) Int. Cl.
*G01N 33/553* (2006.01)
(52) U.S. Cl. .................. 436/525; 436/173; 436/164
(58) Field of Classification Search .................. 436/525, 436/164, 173, 578, 801, 805, 1; 435/7.93, 435/7.94, 7.95
See application file for complete search history.

(56) References Cited

U.S. PATENT DOCUMENTS

| 5,252,459 A | * | 10/1993 | Tarcha et al. | ................. | 435/6 |
| 5,266,498 A |   | 11/1993 | Tarcha et al. |                  |       |
| 5,376,556 A | * | 12/1994 | Tarcha et al. | ................. | 436/525 |
| 5,445,972 A | * | 8/1995  | Tarcha et al. | ................. | 436/544 |
| 5,567,628 A | * | 10/1996 | Tarcha et al. | ................. | 436/525 |
| 6,319,670 B1 | * | 11/2001 | Sigal et al. |                  | 435/6 |

FOREIGN PATENT DOCUMENTS

WO    WO 99/44065    9/1999

OTHER PUBLICATIONS

C.R. Martin and D.T. Mitchell, "Nanomaterials in Analytical Chemistry," *Analytical Chemistry News & Features*, pp. 322-327 (May 1, 1998).
S. Nie and S.R. Emory, "Probing Single Molecules and Single Nanoparticles by Surface-Enhanced Raman Scattering," *Science*, 275:1102-1106 (1997).

* cited by examiner

*Primary Examiner*—Jacob Cheu
*Assistant Examiner*—Pensee T Do
(74) *Attorney, Agent, or Firm*—McKee, Voorhees & Sease, P.L.C.

(57) ABSTRACT

The present invention provides a new class of Raman-active reagents for use in biological and other applications, as well as methods and kits for their use and manufacture. Each reagent includes a Raman-active reporter molecule, a binding molecule, and a surface enhancing particle capable of causing surface enhanced Raman scattering (SERS). The Raman-active reporter molecule and the binding molecule are affixed to the particle to give both a strong SERS signal and to provide biological functionality, i.e. antigen or drug recognition. The Raman-active reagents can function as an alternative to fluorescence-labeled reagents, with advantages in detection including signal stability, sensitivity, and the ability to simultaneously detect several biological materials. The Raman-active reagents also have a wide range of applications, especially in clinical fields (e.g., immunoassays, imaging, and drug screening).

21 Claims, 6 Drawing Sheets

(a) Co-immobilization approach (b) Covalent linking approach (a) Creation of capture antibody surface (b) Exposure to analyte (c) Development with reporter labeled immunogold

RAMAN-ACTIVE REAGENTS AND THE USE THEREOF

CROSS-REFERENCE TO RELATED APPLICATIONS

This application claims the benefit of U.S. Provisional Application 60/234,608, filed Sep. 22, 2000.

STATEMENT REGARDING FEDERALLY SPONSORED RESEARCH OR DEVELOPMENT

None.

BACKGROUND OF THE INVENTION

Many assays exist for detecting and measuring analytes of small quantity in the presence of a large volume of other substances. Such assays typically make use of the high binding affinity between the analyte (the substance to be detected or measured) and a second molecule having a high degree of specificity for binding to that analyte. These assays are often referred to as ligand-binding assays.

One of the most common ligand-binding assays are immunoassays. Immunoassays typically employ an antigen and an antibody which specifically binds to the antigen to form an antibody/antigen complex. In order to measure the extent of the antibody/antigen binding, one member of the complex is generally labeled or tagged with a traceable substance. The presence of the traceable substance, and hence the presence of the antibody or antigen to which it is attached, may then be detected or measured using a variety of different techniques depending upon the unique characteristics of the label employed. These techniques may include an analysis and measurement of scintillation counting, fluorescence, absorption, electrochemistry, chemiluminescence, Rayleigh scattering and Raman scattering. Of these techniques, fluorescence spectroscopy has been one of the most widely used readout methods, primarily because of its high sensitivity.

Although fluorescence spectroscopy has seen substantial use in scientific research and clinical diagnostics, there are disadvantages in using fluorescence spectroscopy. For instance, the different types of fluorescent molecules used in fluorescence spectroscopy typically require excitation with photons of differing wavelengths. Therefore, if the detection of multiple fluorescent molecules is desired in a single sample, multiple light sources may be required. If a single light source is used, there will often exist a spectral overlap between the emission of the different fluorescent molecules such that reliable individual and quantitative detection of multiple analytes in a single sample is limited.

Today, many assays require the concomitant determination of more than one analyte in a single test sample (e.g., the screening of cancer markers, such as α-fetoprotein and carcinoembryonic antigen). There are two general approaches to assaying multiple analytes in a single sample. One approach immobilizes different binding molecules on a solid support at spatially separated addresses. Multiple analytes can then be detected using the same label, with identification based on address location. Alternatively, different labels can be used to detect multiple analytes simultaneously in the same spatial area. In this case, each analyte obtains its own distinct label.

We have explored Raman spectroscopy as an alternative to fluorescence spectroscopy. Raman spectroscopy measures the level of Raman scattering induced by the application of a radiation source, i.e. light source, on an analyte. The light incident on the analyte is scattered due to excitation of electrons in the analyte. "Raman" scattering occurs when the excited electron returns to an energy level other than that from which it came, resulting in a change in the wavelength of the scattered light and giving rise to a series of spectral lines at both higher and lower frequencies than that of the incident light. The series of spectral lines is generally called the Raman spectrum.

Conventional Raman spectroscopy usually lacks sufficient sensitivity for use as a readout method for immunoassays. Raman spectroscopy is also unsuccessful for fluorescent materials due to the broad fluorescence emission bands tend to swamp the weaker Raman bands.

However, a modified form of Raman spectroscopy based on "surface enhanced" Raman scattering (SERS) has proved to be more sensitive and thus of more general use. In the SERS form of Raman spectroscopy, the analyte whose spectrum is being recorded is closely associated with a roughened metal surface. This close association leads to a large increase in detection sensitivity, the effect being greater the closer the analyte sits to the metal surface.

The manner in which surface enhancement occurs is not yet fully understood, but it is thought that the incident light excites conduction electrons in roughened metal surfaces or particles, generating a plasma resonance (plasmon). As a result, the electromagnetic field in the vicinity of the metal surface is greatly amplified, giving rise to enhanced Raman scattering in molecules located close to the surface.

Surprisingly, there have been only a few reports on the application of SERS for detection in immunoassays. Two of these approaches used a sandwich-type assay, which coupled surface and resonance enhancements. In particular, Rohr et al., *Anal. Biochem.* 1989, 182, 388, used labeled detection antibodies and roughened silver films coated with a capture antibody (see also U.S. Pat. No. 5,266,498 to Tarch et al.), and Dou et al., *Anal. Chem.* 1997, 69, 1492, exploited the adsorption on silver colloids of an enymatically amplified product. Another approach by White et al., International Application Publication No. WO 99/44065, employs an immunoassay based on the displacement of SERS and surface enhanced resonance Raman (SERRS) active analyte analogs which are modified so as to have particular SERS and SERRS surface seeking properties. Upon introduction of a sample, the analyte analogs are displaced by the analyte of interest in the sample and exposed to a SERS or SERRS surface, such as an etched or roughened surface, a metal sol or an aggregation of metal colloid particles. Raman spectroscopy is then performed to detect the displaced analyte analog associated with the SERS or SERRS surface to determine the presence or quantity of the analyte in the sample.

A major barrier that prohibits using SERS for the direct detection of biological samples is that the surface enhancement effect diminishes rapidly with increasing distance from the metallic surfaces. In other words, strong SERS signals are observed only if the scattering centers are brought into close proximity (<100 nm) to the surface. In addition, although Raman spectra of biomolecules can be obtained on silver surfaces when coupling SERS and resonance enhanced scattering, the spectra are usually lacking of sufficient chemical content and/or signal amplitude to be used for immunoassay purposes.

We have overcome these barriers by developing a novel class of Raman-active reagents having both Raman-active reporter molecules and binding molecules integrated with each other on the same SERS surface. In each of the above systems, the SERS or SERRS surface and the Raman-active molecule are not integrated with each other, but are merely placed in close proximity to each other by the combination of an analyte sandwiched between an antibody immobilized on the enhancing surface and an antibody attached to a Raman-active molecule, or the combination of the SERS or SERRS surface with a particular SERS or SERRS surface seeking group coupled to an analyte analog and a Raman-active molecule, after exposure to the sample.

BRIEF SUMMARY OF THE INVENTION

The present invention is summarized as a novel class of Raman-active reagents for use in biological and other applications, as well as methods and kits for their use and manufacture.

The Raman-active reagents each include a Raman-active reporter molecule, a binding molecule, and a surface enhancing particle capable of causing surface enhanced Raman scattering. The Raman-active reporter molecule and the binding molecule are operably linked to the particle to give both a strong surface enhanced Raman scattering (SERS) signal and to provide biological functionality, i.e. antigen or drug recognition. The Raman-active reporter molecule and the binding molecule may be either directly linked to the surface enhancing particle or indirectly linked to the surface enhancing particle by way of a linker molecule. In one embodiment, the Raman-active reporter molecule and the binding molecule are each independently linked to the surface enhancing particle. In a second embodiment, the binding molecule is operably linked to the Raman-active reporter molecule, which is operably linked to the surface enhancing particle. Other variations are possible.

The Raman-active reagents may be employed to determine the presence or amount of a target analyte in a test sample by use of the binding specificity of the binding molecule for the target analyte, or a portion thereof, and the generation and measurement of an SERS signal induced by the application of a radiation onto the reagent/analyte complex. The Raman-active reagents may be used, for example, in clinical, forensic, and water quality testing labs for the detection of drugs, pesticides, microbial toxins, hormones and biologically important proteins, industrial chemicals, explosives, trace metals, etc.

The Raman-active reagents may be manufactured in the lab or provided to the user in the form of a kit. The kit may include a previously prepared Raman-active reagent, or the ingredients for manufacturing the Raman-active reagents in the lab. The kit may also include ingredients that minimize nonspecific binding and ingredients that stabilize the reagent to extend its shelf life. In addition, the kit may include a capture substrate covered with binding molecules to immobilize analytes for subsequent detection with the Raman-active reagent. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption.

In one embodiment, the Raman-active reagents are manufactured by coimmobilizing the Raman-active reporter molecules and the binding molecules to metal colloid particles. In the case of gold particles, the reporter molecules can be covalently linked to the particle through thiol functionalities on the reporter molecules. Binding molecules, for example, antibodies, will spontaneously associate with unreacted areas of the particle to form a Raman-active reagent for antigen detection. In a second embodiment, the Raman-active reagents are manufactured by covalently linking the Raman-active reporter molecules to the surface enhancing particle, and by covalently linking the binding molecules to the Raman-active reporter molecules.

It is one object of the present invention to provide a new class of labeling reagents as an alternative to fluorescence-labeled reagents. It is also an object of the present invention to provide a new class of labeling reagents capable of simultaneously detecting multiple analytes in a single test sample.

The Raman-active reagents of the present invention serve as an alternative to fluorescence-labeled reagents, with advantages in detection including signal stability, sensitivity, and the ability to simultaneously detect several analytes in a single test sample. Because of the ability to simultaneously detect several analytes in a single test sample, faster analysis speeds and reduced labor costs may be obtained.

Other objects, features and advantages of the present invention will be apparent in the following Detailed Description of the Invention when read in conjunction with the accompanying drawings, examples and claims.

DETAILED DESCRIPTION OF THE INVENTION

Figure 1:
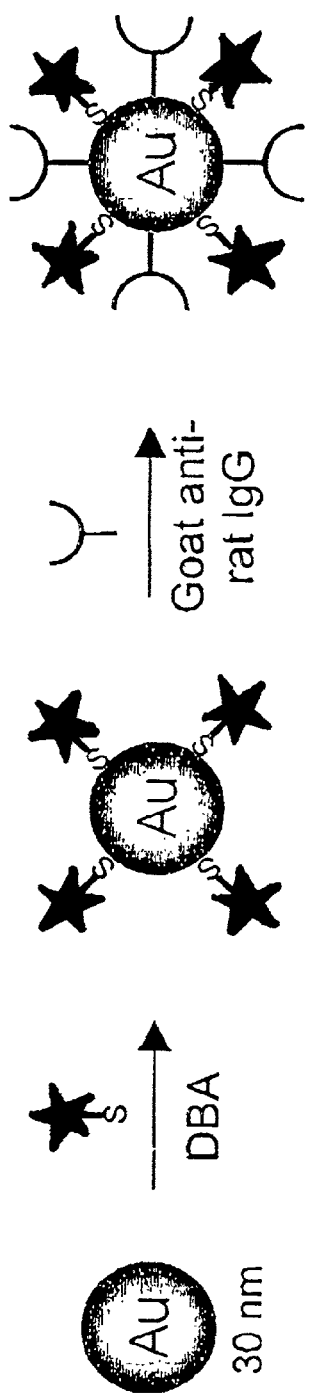
FIG. 1 illustrates two possible methods for preparing Raman-active immunogold reagents.
Figure 1:
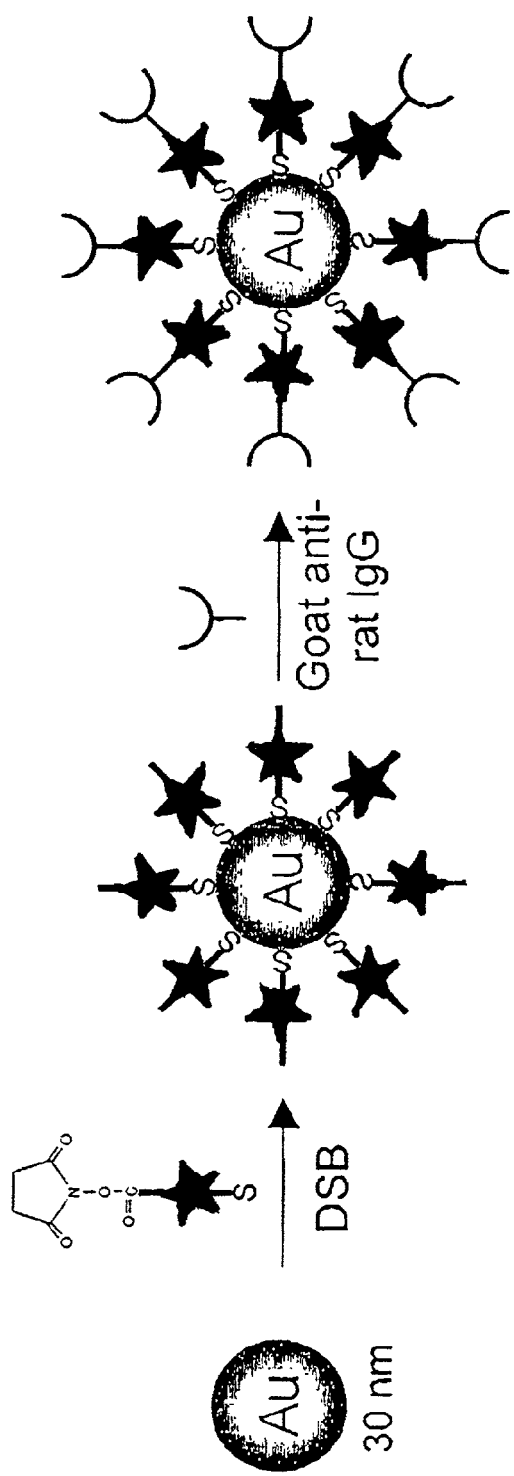

The present invention provides a novel class of Raman-active reagents for use in determining the presence or amount of a target analyte in a test sample. Also provided are particular methods and kits for using the Raman-active reagents of the present invention, as well as certain novel, preferred, methods for their manufacture.

The Raman-active reagents according to the present invention comprise a Raman-active reporter molecule, a binding molecule, and a surface enhancing particle capable of causing surface enhanced Raman scattering. The Raman-active reporter molecule and the biological binder are operably linked, either directly or indirectly, to the surface enhancing particle to give both a strong surface enhanced Raman scattering (SERS) signal and specific binding affinity to a target analyte. The Raman-active reporter molecule and the binding molecule may be either directly linked to the surface enhancing particle or indirectly linked to the surface enhancing particle by way of a linker molecule. The Raman-active reporter molecule and the binding molecule may be independently linked to the surface enhancing particle, or the binding molecule may be operably linked to the Raman-active reporter molecule, which is operably linked to the surface enhancing particle.

The term "surface enhancing particle" is defined herein to include particles capable of causing surface enhanced Raman scattering. Particles capable of causing surface enhanced Raman scattering are well known in the art and generally include, without limitation, particles of metallic materials such as gold, silver, copper, platinum, aluminum, gallium, indium, zinc, cadmium, lithium and sodium. The particles may also include, without limitation, other inert support structures of silica, plastic, glass, carbon, ceramics, or other materials, including magnetic materials, coated with a metallic material capable of causing surface enhanced Raman scattering, such as the metallic materials listed above.

The particles used in the present invention are colloid particles. The colloid particles are preferably of a uniform and desired size and shape and aggregated in a controlled manner so as to be stable against possible self-aggregation. Processes for preparing unaggregated colloids are well known in the art and typically involve, for example, the reduction of a metal salt (e.g., silver nitrate) with a reducing agent (e.g., citrate) to form a stable microcrystalline suspension. The colloid particles can be of any size as long as they give rise to an SERS signal. For example, the colloid particles may be less than 1000 nm in diameter, and preferably less than 100 nm in diameter.

In the preferred embodiment, the surface enhancing particles are metallic nanoparticles. The large surface enhancement observed on metallic nanoparticles results in SERS intensities that can be comparable to or even exceeding those for fluorescence. Such a level of enhancement, which may lead to a high detection sensitivity, together with the ease of handling, make metallic nanoparticles more promising than most other types of SERS substrates for use in ligand-binding assay applications. Of the various metallic nanoparticles, gold colloids is preferred over silver colloids, despite the fact that silver colloids provide larger enhancements than gold. This is because the greatest Raman enhancements with gold particles are produced with longer wavelength excitation light. This makes it possible to minimize the generation of sample fluorescence, which may interfere with the measurement of the Raman scattering.

The term "Raman-active reporter molecule" is defined to include any one of a number of molecules with distinctive Raman scattering patterns. Various molecules with distinctive Raman scattering patterns are well known in the art. Examples of such molecules include, but is not limited to, dithiobisbenzonic acid (DBA), 4-mercaptobenzoic acid (MBA), 2-naphthalenethiol (NT), thiophenol (TP), direct red 81, Chicago sky blue, 4,4'-dithiobis(succinimidylbenzoate) (DSB), p-dimethylaminoazobenzene, 1,5-difluoro-2,4-dinitrobenzene, 4-(4-Aminophenylazo)phenylarsonic acid monosodium salt, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

The term "binding molecule" is defined to include any molecule having a binding specificity and avidity for a molecular component of a target analyte, or which is associated with a target analyte. In general, binding molecules are known to those skilled in the art and typically include, without limitation, lectins (including fragments or derivatives thereof which retain binding function), monoclonal and polyclonal antibodies (including immunoreactive fragments or derivatives derived therefrom, which fragments retain all or a portion of the binding function of the antibody), peptides, haptens, aptamers, and nucleic acid molecules (including single stranded RNA, single-stranded DNA, or single-stranded nucleic acid hybrids), and any fragments and derivatives thereof. Crown ethers, cyclodextrins, cryptands, calixarenes, and many other types of ligands could also be used.

The term "target analyte" is defined to include a molecule of an organic or inorganic nature, the presence and/or quantity of which is being tested for, which contains a molecular component (e.g., ligand or sequence or epitope or domain or portion or chemical group or reactive functionality or determinant) for which a binding molecule has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, antibody, drug, therapeutic, toxin, inorganic chemical, organic chemical, a substrate and the like.

The term "test sample" means a sample to be tested for the presence or amount of a target analyte. The sample may include a target analyte or be free from the presence of the target analyte.

The term "operably linked" is defined to mean a linkage between two different molecules, or a molecule and a particle, of sufficient stability for the purposes of signal enhancement and detection according to the present invention. As known to those skilled in the art, and as will be more apparent by the following embodiments, there are several methods and compositions in which two or more molecules, or a molecule and a particle, may be operably linked utilizing reactive functionalities. Reactive functionalities include, but are not limited to, bifunctional reagents, linker molecules, biotin, avidin, free chemical groups (e.g., thiol, or carboxyl, hydroxyl, amino, amine, sulfo, phosphine, selenide, etc.), and reactive chemical groups (reactive with free chemical groups).

The term "linker" is defined to refer to a compound or moiety that acts as a molecular bridge to operably link two different molecules, or a molecule and a particle, wherein one portion of the linker is operably linked to a first molecule, and wherein another portion of the linker is operably linked to a second molecule or particle. The two different molecules, or the molecule and particle, may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homobifunctional linkers and heterobifunctional linkers. As an illustrative example, a linker may comprise a carboxylic acid that has been activated by conversion to its acid chloride to react with an amino acid (e.g., lysine) residue of a binding molecule comprising a monoclonal antibody, and a thiol reactive group to link with the particle or the Raman-active reporter molecule.

Heterobifunctional linkers are well known to those skilled in the art and generally contain one end having a first molecule, and an opposite end having a second reactive functionality to specifically link to a second molecule. Heterobiofunctional photo-reactive linkers (e.g., phenylazides containing a cleavable disulfide bond) are also well known in the art and may be employed as linkers in accordance with the present invention. For example, a sulfosuccinimidyl-2-(p-azido salicylamido) ethyl-1,3'-dithiopropionate contains a N-hydroxysuccinimidyl azide (upon photolysis) reacts with any amino acid.

The linker may further comprise a protective group which blocks reactivity with a functional group on the linker which is used to react with and bind to a molecule or particle to be linked. A deprotection reaction may involve contacting the linker to one or more conditions and/or reagents which remove the protective group, thereby exposing the function group to interact with the molecule to be linked. Depending on the nature of the protective group, deprotection can be achieved by various methods known in the art, including, but not limited to, photolysis, acidolysis, hydrolysis, and the like. Depending on such factors as the molecules and particles to be linked, and the conditions in which the method of detection is performed, the linker may vary in length and composition for optimizing such properties as flexibility, stability, and resistance to certain chemical and/or temperature parameters. For example, short linkers of sufficient flexibility include, without limitation, linkers having from 2 to 10 carbon atoms (see, e.g., U.S. Pat. No. 5,817,795).

Any two molecules having an affinity for each other may comprise the reagent/analyte complex according to the present invention. Examples of ligand-binding systems include: antibodies and antigens; hormones and their receptors; lectins and the complex carbohydrates to which they bind; effector molecules and their receptors; complimentary nucleotide sequences; binding molecules designed through molecular modeling and synthesized specifically to bind another molecule, and molecules with mutual affinity to each other, such as avidin and biotin.

In one embodiment, the Raman-active reporter molecule and the binding molecule are each independently linked to the surface-enhancing particle. The Raman-active reporter molecule and the binding molecule may be either directly linked to the surface enhancing particle or indirectly linked to the surface enhancing particle by way of a linker molecule.

In another embodiment, the binding molecule is operably linked to the Raman-active reporter molecule, which is operably linked to the surface enhancing particle. The Raman-active reporter molecule and the binding molecule may be either directly linked to the surface enhancing particle or indirectly linked to the surface enhancing particle by way of a linker molecule.

The Raman-active reagents of the present invention may be manufactured in the lab or provided to the user in the form of a kit. The kit may include a previously prepared Raman-active reagent, or the ingredients for manufacturing the Raman-active reagents as described above. The kit may also include ingredients that minimize nonspecific binding (nonspecific binding ingredient) and ingredients that stabilize the reagent (stabilizing ingredient) to extend its shelf life. Various nonspecific binding ingredients and stabilizing ingredients effective in use with the present invention are well known in the art. In addition, the kit may include a capture substrate covered with binding molecules to immobilize analytes for subsequent detection with the Raman-active reagent. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption. For example, surfactants, blocking agents, and buffers may be added.

Raman reporter-labeled immunogold probes can be prepared in many different ways. For example, as depicted in FIG. 1(a) (the co-immobilization approach), an uncoated gold nanoparticle is labeled with Raman-active reporter molecules through the spontaneous adsorption of thiol-containing reporter molecules on gold, and then integrated with antibodies. The amount of thiol is chosen to coat only a portion of the nanoparticle surface and to leave exposed portions of the nanoparticle surface available for antibody immobilization. The antibodies are subsequently immobilized on the uncoated portion of the reporter-labeled nanoparticle through a combination of ionic and hydrophobic interactions.

In a second example, as depicted in FIG. 1(b) (the covalent linker approach), an uncoated gold nanoparticle is labeled with Raman-active reporter molecules, which are then covalently linked to antibodies. The Raman-active reporter molecule not only carries thiol or disulfide groups for immobilization on the gold nanoparticle, it also contains a succinimide ester functional group (i.e., a coupling reagent) for the covalent linking of an antibody. The covalent linker approach enhances the Raman reporter coverage and ultimately its sensitivity. Because the antibodies are covalently linked to the nanoparticles, the cross reactivity between antibodies on different nanoparticles is reduced, and hence the probe specificity in the multi-analyte application is improved.

The Raman-active reagents of the present invention determine the presence or amount of a target analyte, if present in a test sample, by the binding specificity of the binding molecule for the target analyte, or a portion thereof, and the generation and measurement of a SERS signal induced by the application of electromagnetic radiation onto the reagent/analyte combination. The Raman-active reagents may be used in clinics or forensic labs for the detection of drugs, pesticides, microbial toxins, hormones and biologically important proteins, industrial chemicals, explosives, pesticides, chlorophenols and other pollutants in soils, water, air, biological materials and other matrices. Such analysis may include in-situ testing methods (i.e., those not requiring any separation of the analytes from the sample prior to either their analysis or detection), as well as other in vivo, in vitro, or ex vivo methods.

The detection or measurement of target analytes using the Raman-active reagents according to the present invention may be performed using any one of a number of assaying techniques known in the art. In general, a test sample is placed in contact with a Raman-active reagent of the present invention under suitable conditions to allow the binding molecule to specifically bind to the target analyte, thus forming a reagent/analyte complex. The sample containing the reagent/analyte complex is then exposed to an excitation source (e.g., light source) that is suitable for exciting the Raman-active reporter molecule to induce surface enhanced Raman scattering. The intensity of the Raman scattering signal can then be measured to determine the presence or amount of the target analyte in the test sample. Absence of a Raman scattering signal is indicative of the absence of the target analyte in the test sample.

Techniques for detecting Raman scattering are well known in the art. The primary measurement is one of light scattering intensity at particular wavelengths. Neither the angle of the incident beam nor the position of the detector is critical. With colloidal suspensions, detection is often at an angle of 90° to the incident beam. The intensity of the Raman scattering signals must be measured against an intense background from the excitation source. As such, the use of Raman-active report molecules with large Stokes shifts is preferred.

Several devices are suitable for collecting SERS signals, including fiber-optic waveguides, wavelength selective mirrors, and holographic optical elements for scattered light detection. The choice of the detector will largely depend on the sensitivity of detection required to carry out a particular assay. The intensity of the signal may be measured using a silicon photodiode, a charge coupled device (CCD), photographic film, or photomultiplier tubes arranged either singly or in series for cascade amplification of the signal. Photon counting electronics can also be used for sensitive detection.

Analysis of the SERS spectrum will typically include the use of some form of data processor such as a computer. Raman signals consist of a series of distinct spectral lines of varying intensity. The frequencies and relative intensities of these spectral lines are specific to each Raman-active reporter molecule being detected such that each Raman-active reporter has a distinct "fingerprint". The manner in which this fingerprint is analyzed will depend primarily on the purpose of the detection. If a SERS analyzer is being used to selectively detect one or more analytes out of a test sample containing multiple analytes, then an analysis of the entire fingerprint for each reporter molecule may be necessary to make a reliable identification. However, if the analyzer is being used to quantify the detection of one or several labels, each of which has a unique spectral line, then an analysis of only the unique spectral line may be necessary.

The excitation source may be any source capable of exciting the Raman-active reporter molecule to induce Raman scattering. Typically, excitation will be carried out using incident light from a laser having a frequency in the visible spectrum. However, it is possible to envision situations in which other frequencies might be used, for example, in the ultraviolet or near-infrared ranges. The selection and tuning of the excitation source, with the appropriate frequency and power, will be well within the capabilities of one skilled in the art and will depend on the reporter molecule, surface enhancing particle and target analyte employed. In the preferred embodiment, a laser serves as the excitation source. The laser may be an inexpensive type such as a helium-neon or diode laser. Preferably, a diode laser is used at or near the IR spectrum, minimizing fluorescence interference. Lamps may also be used as the excitation source. Direct illumination of the surface or by evanescent waves from a waveguide beneath the plasmon-active surface may also employed to induce a SERS affect.

Figure 3:
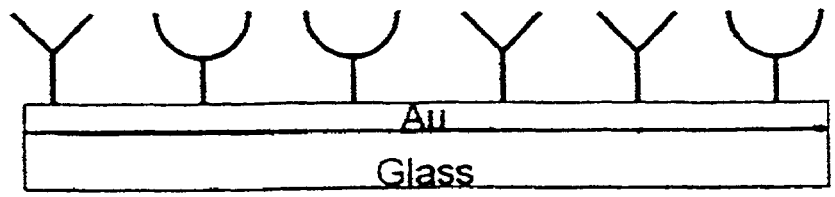
FIG. 3 illustrates an example of a sandwich assay employing Raman-active reagents of the present invention.
Figure 3:
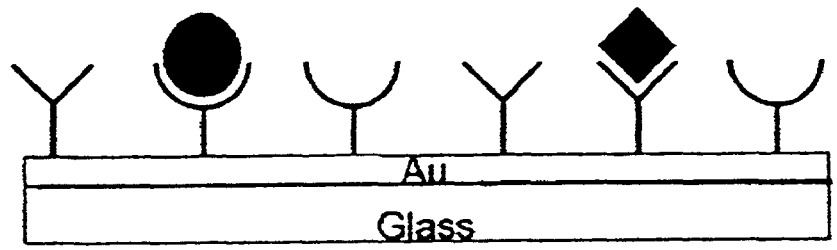
Figure 3:
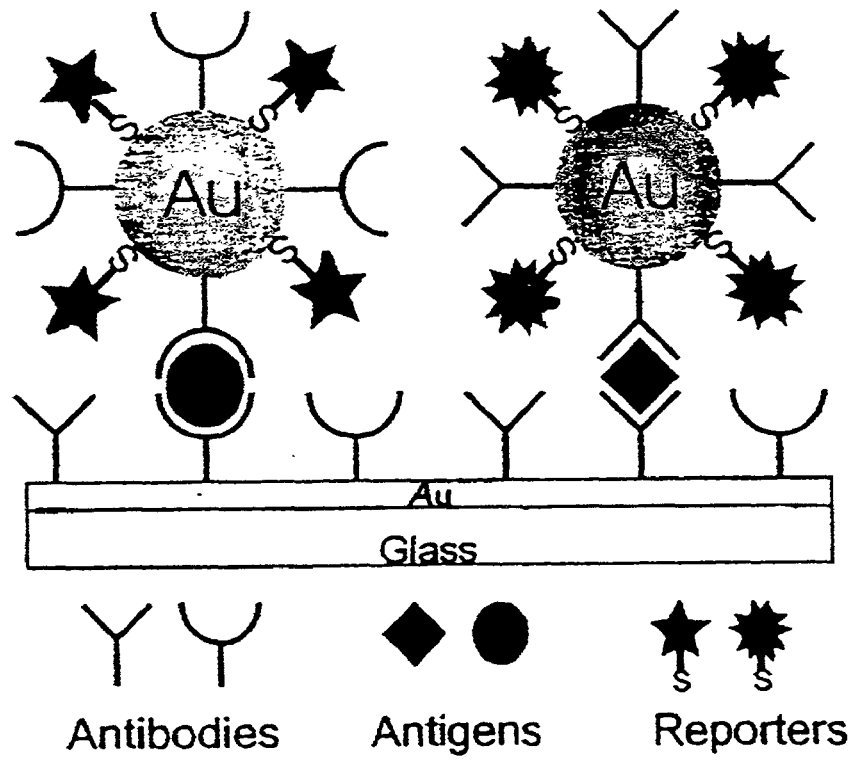

An illustration of a typical SERS measurement system is depicted in FIG. 3.

In the preferred embodiment, the test sample may be placed in contact with a capture substrate covered with binding molecules that selectively immobilize analytes for subsequent detection with the Raman-active reagent. This substrate is then treated with the Raman-active reagent under suitable conditions to allow the Raman-active reagent binding molecule to specifically bind to the target analyte, forming the reagent/analyte complex. FIG. 3 illustrates one type of assay employing such a method. In this example, a different Raman-active reporter molecule is associated with a different antibody as different probes, with the presence of different antigens detected by the characteristic Raman bands of the reporters. In an alternative embodiment, the test sample may be contacted with the Raman-active reagent under suitable conditions to allow the Raman-active reagent binding molecule to specifically bind to the target analyte, forming the reagent/analyte complex, prior to its capture by the substrate.

The substrate may take the form of a generally flat surfaces (e.g., strips, slides, gene chips, etc.) or inert support structures of silica, carbon, plastic, glass, paper or other materials which may be in the form of macroscopically flat or textured pieces, slides, strips, spheroids or fibers capable of supporting the reagent/analyte complex. Analytes and/or the reagent/analyte complex may bind to the substrate by direct adsorption, adsorption through a linker covalently attached to either the particle or the reporter molecule, by covalent attachment of the particle or reporter molecule to the substrate directly or through a linker or by intercalation of the distal portion of the linker into the substrate surface, by magnetic attraction to the substrate, or by specifically binding a second binding molecule affixed to the substrate to the target analyte or a molecule operably linked to the particle and having a specific affinity for the second binding molecule. For example, the substrate may include a binding molecule identical to that found on the Raman-active reagent that binds the target analyte, such as in a sandwich assay. Such a system might be employed for the detection of multiple target analytes using a limited number of different Raman-active labels in association with multiple binding molecules. Identification and quantification of the analytes would be accomplished through the measurement of the distinctive spectral fingerprints of the Raman-active labels provided for each analyte. Alternatively, the substrate may contain address locations for the various analytes with the specific binding molecule identified by the address location rather than by its spectral fingerprint. This system may also be employed for separating the target analyte from the test sample.

In another embodiment, the method may further comprise exposing the test sample to a magnetic force that separates the reagent/analyte complex from the test sample. Such separation may occur if the surface-enhancing particle comprises of a material that is responsive to a magnetic force. In this case, the magnetic-responsive material is likely to be coated with a metallic material capable of emitting a SERS signal. Upon detection of the SERS signal, the magnetic force may be applied to cause the reagent/analyte complex to be separated from the test sample. In addition, different Raman-active reagents having different Raman-active reporter molecules and binding molecules may be employed to allow for the sorting of multiple target analytes using magnetic forces.

Assay kits for the method of the present invention are also provided. In one preferred embodiment, the assay kit comprises a Raman-active reagent in accordance with the present invention, wherein the Raman-active reagent includes at least one binding molecule having an affinity for a known target analyte. In a second embodiment, a substrate capable of binding the analyte and/or the reagent/analyte complex is provided. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption. For example, surfactants, blocking agents, and buffers may be added.

One aspect of the present invention is that it allows multiple target analytes to be detected from a single test sample. For example, simultaneous detection may be achieved by the use of multiple binding molecules, each specific to a target analyte or a class of target analytes and each associated with a different Raman-active reporter molecule. Because Raman-active vibrational modes usually yield bands one to two orders of magnitude narrower than most fluorescence bands, it is now possible to distinguish a much large number of different Raman labels as compared to fluorescent labels. Alternatively, a single Raman-active reporter molecule may also be employed with identification based on an address location on a substrate, such as a gene chip or screening slide, as is well known in the art.

Because Raman scattering is not affected by oxygen and other quenchers, thus simplifying its use in many different experimental environments, it has potential advantages as a broadly applicable readout method in comparison to the widely used fluorescence detection schemes. In addition, because the SERS signal is less subject to photobleaching, lower detection limits can be obtained by increasing the signal integration time. Raman-active vibrational modes also usually yield bands one to two orders of magnitude narrower than most fluorescence bands, indicating the possibility of distinguishing a much large number of different Raman-active labels than likely with fluorescent labels, and minimizing the need to use special locations for analyte identification.

One argument favoring a fluorescence over a Raman-based detection scheme, in the past, is the inherent detection capability of fluorescence measurements. However, by combining the SERS effect and the use of reporter molecules with a relatively large Raman scattering cross section as extrinsic labels, trace amounts of intrinsically weak Raman scatterers (e.g., antibodies) can be indirectly detected. A detection limit of 0.1 ng/mL has been estimated from recent experiments for the antibody detection. With further optimization, even lower detection limits are expected.

The below Examples include an illustration describing an application of one type of Raman-active gold colloidal reagent (Raman-active reagent) used as a detection reagent in immunoassays. It is envisioned that similar concepts can be developed for other types of assays, target analytes and Raman-active reagents developed in accordance with the present invention, as well as infrared-active colloidal reagents, and in some cases, reagents for fluorescence or electrochemical based assays.

EXAMPLES

Example 1

Synthesis of Raman-Active Reporter Molecule 4,4'-Dithiobis(Succinimidylbenzoate)

The Raman-active reporter molecule 4,4'-dithiobis(succinimidylbenzoate) (DSB) was synthesized following a procedure similar to that used for preparing dithio-bis(succinimidylundecanoate) as described in Wagner et al., *Biophys. J.* 1996, 70, 2052, which is incorporated herein by reference. Briefly, 0.50 g of the reporter molecule dithiobisbenzonic acid (DBA) (1.6 mmol) (Toronto Research Chemicals, Inc), 0.67 g of 1,3-dicyclohexylcarbodiimide (DCCD) (3.2 mmol) (obtained from Aldrich), 0.37 g of N-hydroxysuccinimide (NHS) (3.2 mmol) (obtained from Aldrich), and 60 mL of tetrahydrofuran were added to a 100 mL round-bottom flask equipped with a magnetic stir bar and drying tube. The reaction mixture was stirred at room temperature for three days. The solution was then filtered and the solvent was removed under reduced pressure to give an orange residue. The crude product was dissolved in hot acetone and filtered again. Hexane was added to the filtrate until the solution became cloudy and the product was obtained as an orange powder. H-NMR (300 MHz, CDCl$_3$): δ8.08 (d, 4H), 7.60 (d, 4H), 2.91 (s, 8H). Infrared reflection spectroscopy: 1810 cm$^{-1}$ ($v_{(C=O)}$ of the ester), 1772 cm$^{-1}$ ($v_{s(C=O)}$ of the succinimide), 1746 cm$^{-1}$ ($v_{as(C=O)}$ of the succinimide), 1585 cm$^{-1}$ ($v_{(C=C)}$ of the benzene ring).

Example 2

Preparation of Raman-Active Reagents Using Co-Immobilization

Raman-active immunogold colloidal reagents were prepared using the co-immobilization approach depicted in FIG. 1(*a*). First, 25 μL of ethanolic Raman reporter solution (0.5 mM DBA) was added to 10 mL of a suspension of uncoated gold colloids (~30 nm diameter, 2×10$^{11}$ particles/mL) (Ted Pella, Inc.). The mixture was allowed to react for 5 hours at room temperature. During this step, the reporter molecules bound via self-assembly onto the colloid surface through the formation of sulfur-gold linkages. We note that this amount of reporter, based on an estimation of the colloidal surface area, will only partially cover the colloid, leaving portions of the uncoated colloidal surface available for protein immobilization. After separating the reporter-labeled colloids from solution by centrifugation at 14,000 g for 4 minutes, the loosely packed, red-colored sediment was resuspended in 10 mL of borate buffer (2 mM, pH 9).

The Raman-active colloids were next immuno-labeled by adding 230 μg of goat anti-rat IgG to 10 mL of the above suspension. The mixture was incubated at 4° C. for 12 hours, during which the IgG protein adsorbed directly onto the exposed colloidal surface through a combination of ionic and hydrophobic interactions. The incubation was followed by centrifugation at 14,000 g for 5 minutes, and the loose sediment of reporter-labeled immunogold was rinsed by resuspending in 2 mM borate buffer and collected after a second centrifugation. Finally, the labeled colloids were suspended in 10 mM tris(hydroxymethyl) aminomethane (Tris)-buffered saline (Tris/HCl, NaCl 10 mM, pH 7.6) giving a concentration of approximately 2×10$^{11}$ particles/mL. Tween 80 (1%) (Aldrich) was also added to the suspension to minimize non-specific adsorption in the assays. The suspensions usually remained uniformly dispersed for 2-3 days when stored at 4° C.

Example 3

Preparation of Raman-Active Reagents Using a Covalent Linking

Raman-active immunogold colloidal reagents were prepared using the covalent linking approach depicted in FIG. 1(*b*). The DSB molecules were used as both Raman reporters and antibody linkers. The succinimide ester group of the DSB molecule can readily react with the primary amine group of an amino acid, such as the lysine, present in antibodies such as IgG to form a covalent bond. As shown in Scheme 2, the preparation of the covalently-linked colloidal reagent follows a process very similar to that used for the co-immobilized reagents. However, with the covalent linking approach, the antibodies indirectly attached to the colloid through the reporter molecules rather than directly adsorbed onto the colloidal surface. Briefly, 25 μl, of a reporter-linker solution (5 mM DSB in CHCl$_3$) was added to 10 mL of bare gold suspension (30 nm) under vigorous agitation. The molecules self-assemble onto the colloid surface, with their succinimide end groups available for protein immobilization. It is noted that this amount of the reporter-linker is estimated to be more than enough to cover the entire colloidal surface. The reporter-linker labeled colloids were centrifuged, and resuspended in the aforementioned borate buffer.

Similar to the co-immobilization approach above, 230 μg of goat anti-rat IgG were added to the 10 mL suspension of the DSB-labeled gold colloids, followed by an incubation at 4° C. for 12 hours. This step covalently couples anti-rat IgG molecule to the colloid surface via amide linkages that are formed by the reactions of its amine groups with the succinimide ester groups of DSB. Finally, the Raman-active immunogold was rinsed and resuspended in Tris buffer, and the final concentration of the colloids was adjusted to approximately $2\times10^{11}$ particles/mL. The suspensions were usually stable for a few weeks when stored at 4° C.

Example 4

UV-Vis Characterization of Gold Island Films

Gold island films were used as SERS-active substrates to examine the scattering properties of the acid-terminated DBA and succinimide-terminated DSB reporters discussed above. Gold films were deposited onto clean glass microscope slides by resistive evaporation at a pressure of less than $1.3\times10^{-4}$ Pa. Gold island films, which were used as the SERS substrates in Raman reporter characterization experiments, were prepared by evaporating approximately 5 nm of gold directly onto the glass substrate. The island films were then derivatized with reporter molecules by immersion in 1 mM DBA (in ethanol) or 1 mM DSB (in chloroform) solutions for 24 hours, and subsequently rinsed with the corresponding neat solvents before SERS characterization. Smooth gold films were prepared by first coating a glass substrate with 15 nm of chromium followed by 300 nm of gold. These substrates were used to prepare capture antibody substrates for the immunoassay experiment described below.

Figure 4:
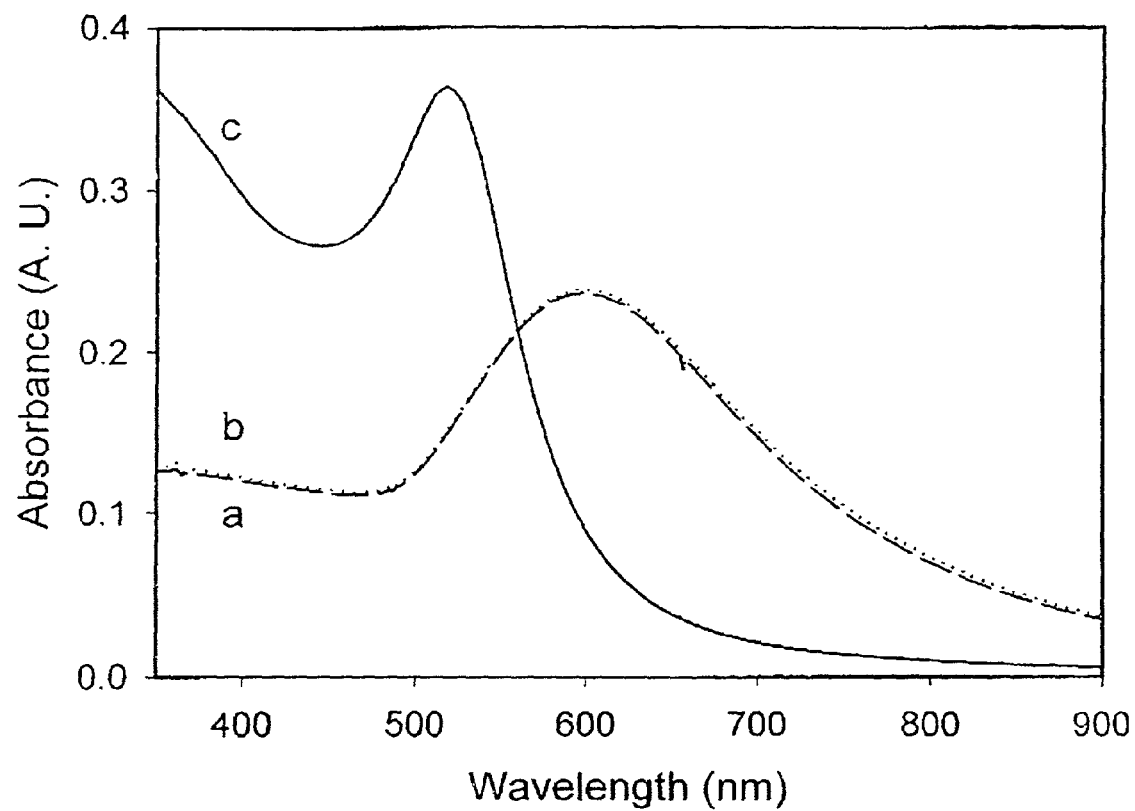
FIG. 4 is a graph illustrating the UV-Vis spectra for SERS substrate characterization.

To minimize differences caused by substrate variability, the gold island films (~5 nm thick) were first examined using UV-Vis spectrometer. FIG. 4 shows the spectra of two such films (spectra a and b) before immersion in the reporter molecule solution. For comparison, spectrum c was collected from 5 nm colloidal gold suspended in aqueous solution. Both island films exhibited a plasmon resonance band with a maximum of 597 nm, while that for colloidal gold was at 519 nm. The plasmon bands from the island films were also wider than that observed from uniformly dispersed 5 nm colloidal gold. The difference in the spectra of the 5 nm-thick gold island films and the 5-nm diameter gold colloid suspension can be explained by the distribution of sizes and shapes of the nanostructures on the two different types of samples. Evaporated gold islands usually have a broad size distribution with different irregular shapes. Colloidal gold, on the other hand, is reported to be more uniform in size and have a near-spherical shape.

It is more important to note that the spectra for the two island films were effectively superimposable. This agreement argues that the average sizes and shapes of the islands on the two substrates were strongly similar. As a result, both substrates should have had similar surface plasmon properties and therefore produce similar magnitudes of surface enhancement for Raman scattering.

Example 5

SERS Characterization of DBA and DSB Reporter Molecules

Figure 2:
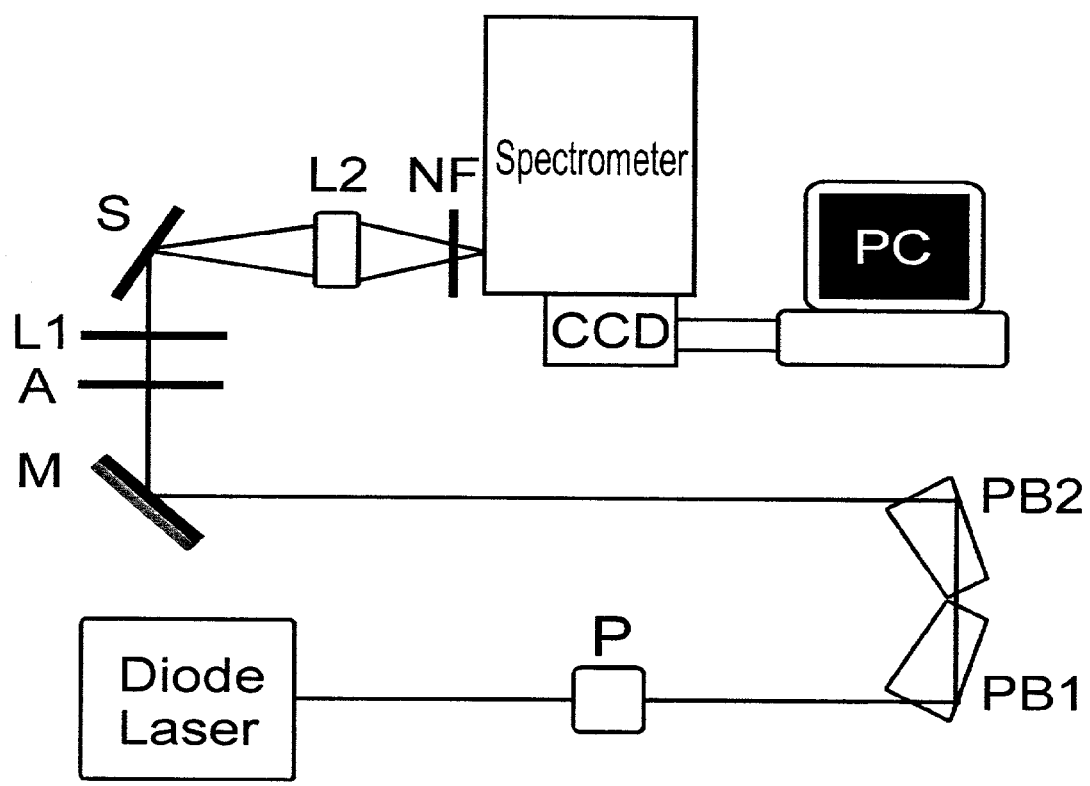
FIG. 2 depicts an illustrative setup for SERS measurements. P: polarization rotator; PB1 and PB2: Pellin Brocha prisms; M: mirror; A: aperture; L1: cylindrical lens; S: sample slide; L2: collection lens; NF: notch filter.

The DBA and DSB reporter molecules were analyzed to determine the difference in the reporter scattering properties as a result of altering the terminal functional groups in the reporter molecule. The experimental setup for the SERS measurements is shown in FIG. 2. The signal was excited with a diode laser (Hitachi HL7851G, Thorlabs) operated at 20° C. and 120 mA. These conditions produced 50 mW of output power at the sample with a wavelength of 785.13 nm. A polarization rotator adjusted the polarization direction of the laser to minimize reflection losses at the Pellin-Brocha prisms. The prisms were used to remove background laser emission. The laser beam was then directed by a mirror through an aperture and focused by a 50-mm focal length cylindrical lens to a 3 mm by 0.25 mm line on the sample surface. The laser beam irradiated the sample at an angle of approximately 60° with respect to the surface normal, and the scattered light was collected and focused onto the entrance slit of the monochromator with a f/2 lens. A holographic notch filter (HSPF-785.0, Kaiser Optical Systems) was used to block the Rayleigh scattered light, while the Raman scattered light passed through the entrance slit (200 μm slit width) of a 300 mm f/4 spectrograph (SpectraPro 300i, Acton Research Corp.) and illuminated onto a 1200 grooves/mm grating. The grating was blazed for 750 nm and produced a nominal dispersion of 2.7 nm/mm. A thinned, back-illuminated, liquid nitrogen-cooled CCD (LN/CCD-1100PB, Princeton Instruments) was controlled by a PC for spectra acquisition. The positions of the reporter molecule Raman bands were determined by calibration using the known band positions of solid naphthalene.

Figure 5:
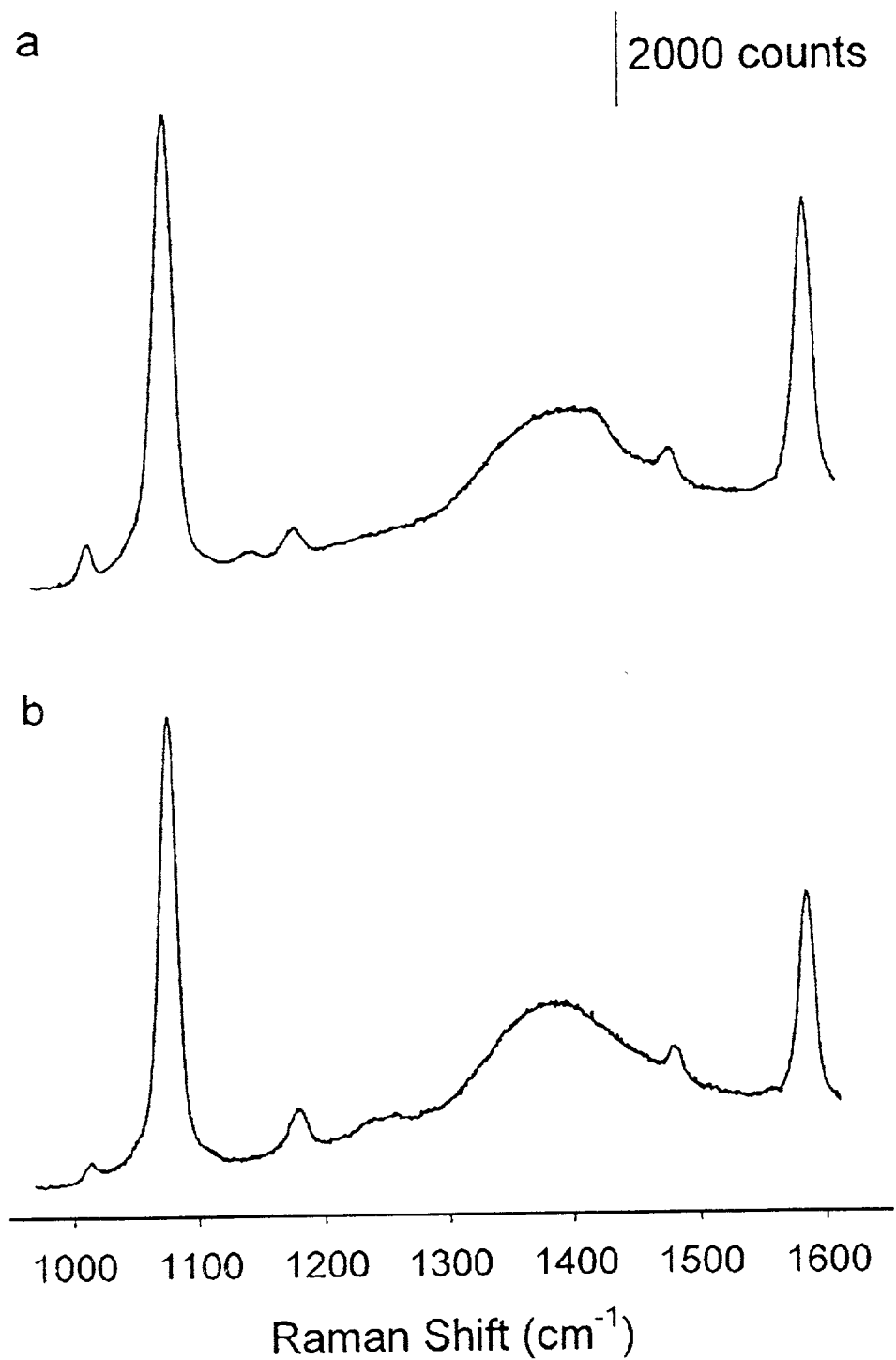
FIG. 5 is a graph illustrating the SERS spectra of dithio-bisbenzonic acid (DBA) and 4,4'-dithiobis(succinimidylbenzoate) (DSB) Raman-active reporter molecules adsorbed on gold island film substrates: (a) DBA, (b) DSB.

SERS spectra (10 second integration time) of self-assembled monolayers of DBA and DSB on the gold island films are shown in FIG. 5. Several strong aromatic vibrational bands from the benzene ring are present within this spectral region. The strongest band at 1075 cm$^{-1}$ is from the aromatic C—H in-plane bending, and another major band at 1585 cm$^{-1}$ is from the C=C ring stretching. To obtain maximum sensitivity, signals at 1075 cm$^{-1}$ were used as readout in both the DBA and DSB-based immunoassays. The similar intensities of the bands in the two spectra of FIG. 5 was consistent with what was expected based on the similarity in the molecular structures of the two types of reporters. It was also noted that the intensity ratios of the peak at 1075 cm$^{-1}$ to the peak 1585 cm$^{-1}$ in the two spectra were slightly different, possibly reflecting the orientation difference of the two types molecules when adsorbed on the surface.

The existence of two additional bands was observed in the DBA spectrum, both with very low intensities. The band at 1420 cm$^{-1}$, which appears as a shoulder on the broad glass band (i.e., Si—O stretches) around 1390 cm$^{-1}$, is strongly characteristic of a COO$^-$ symmetric vibration, while the 1150 cm$^{-1}$ band in the DBA spectra is tentatively assigned to a C—OH stretching mode. In summary, replacing the carboxylate group with succinimide group had only a minor influence on SERS signal derived from the benzene structure in the DBA and DSB molecules. The Raman signatures from the carboxylate group diminished in the DSB spectrum, verifying the synthesis product.

Example 6

Preparation of Capture Antibody Substrates

Glass microscopes slides were soaked in a dilute surfactant solution (Micro, Cole-parmer) for 12 hours, rinsed with deionized water and ethanol, and dried in a stream of nitrogen. The slides were then coated with 15 nm of chromium, followed by 300 nm of gold by resistive evaporation at a pressure of less than $1\times10^{-4}$ Pa. The gold substrates were next cut into 1 cm×1 cm sections and immersed in a 1 mM ethanolic solution of thioctic acid for approximately 12 hours to form a carboxylic acid-terminated monolayer.

The immobilization of the IgG proteins was accomplished by first immersing the monolayer-modified substrates into 1% (w/w) 1-ethyl-3-[3-(dimethylamino)propyl]carbodiimide (EDC) (Aldrich) in anhydrous acetonitrile for 5 hours. This step activates the free carboxyl groups of thioctic acid by forming on O-acylurea intermediate with the EDC. The activated surface was then modified with capture antibody by pipetting 100 μL of goat anti-rat IgG (100 μg/mL, 0.1 M borate buffer, pH 9) (Pierce) onto approximately 1-cm² of the activated substrate. This reaction was allowed to progress at 4° C. for 12 hours. Finally, the antibody-coated substrates were rinsed with deionized water, and quickly dried under a stream of argon. All assays were conducted using freshly prepared substrates.

Example 7

Dose-Response Curves

Dose-response curves were constructed based on the results of a set of sandwich assays. Samples containing Rat IgG (Pierce) as a model antigen were prepared at concentrations ranging from 0.01 ng/mL to 1 mg/mL in 50 mM PBS buffer ($KH_2PO_4/K_2HPO_4$, 150 mM NaCl, pH=7.6). A 100 μL aliquot of each sample solution was pipetted onto the separate capture antibody substrates described above, and allowed to react for 1 hour at room temperature. After rinsing with copious amounts of water, the substrates were then exposed to 100 μL of reporter-labeled immunogold solution for 3 hours. All substrates were rinsed with deionized water and dried under argon before SERS characterization.

The detection approach relied solely on the SERS effect by utilizing the immunogold colloids labeled with Raman-active reporter molecules as detection reagents. In this approach, gold colloids were labeled with both antibodies for bio-recognition and Raman-active reporter molecules for signal transduction. A key feature of this concept is that the scattering center of the label is positioned in close proximity to the colloid surface, which strongly enhances the signal. The presence of the antigen was therefore recognized by its detection antibody, and the SERS signal of the co-immobilized Raman active species reported the ligation of the antibody with the antigen.

Figure 6:
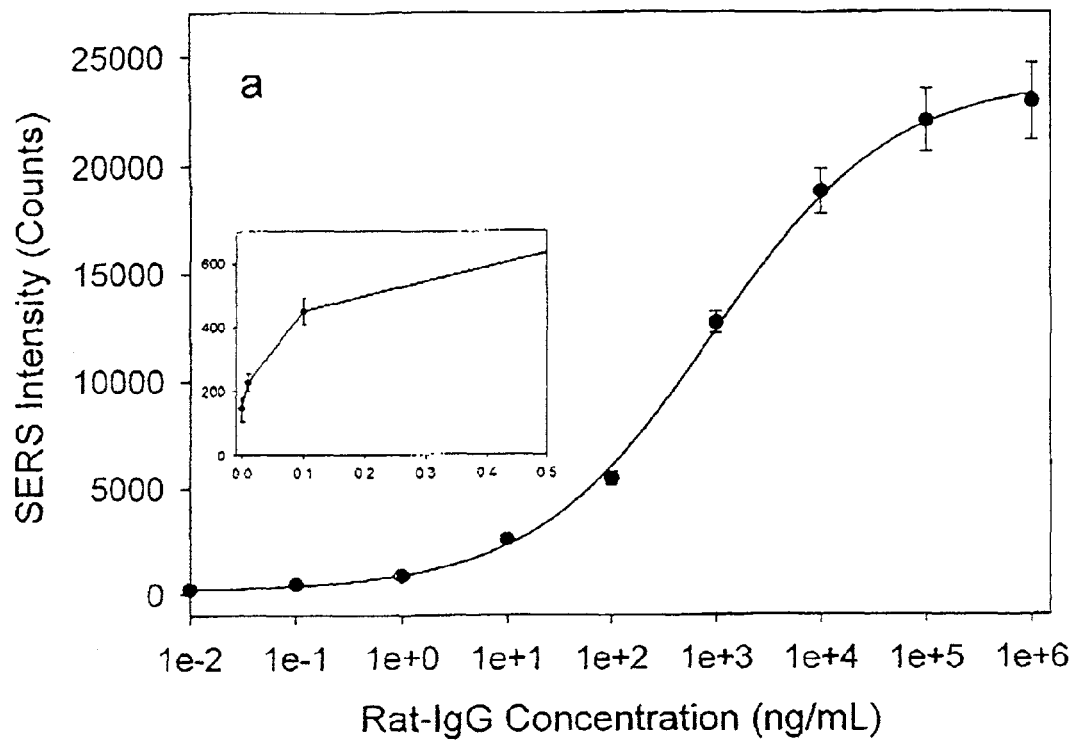
FIG. 6 is a graph illustrating the dose-response curves of the intensity of the strongest SERS band (1075 cm$^{-1}$) versus the rat IgG concentration: (a) using the colloidal detection reagent prepared via the co-immobilized approach, (b) using the colloidal detection reagent prepared via the covalent linking approach.
Figure 6:
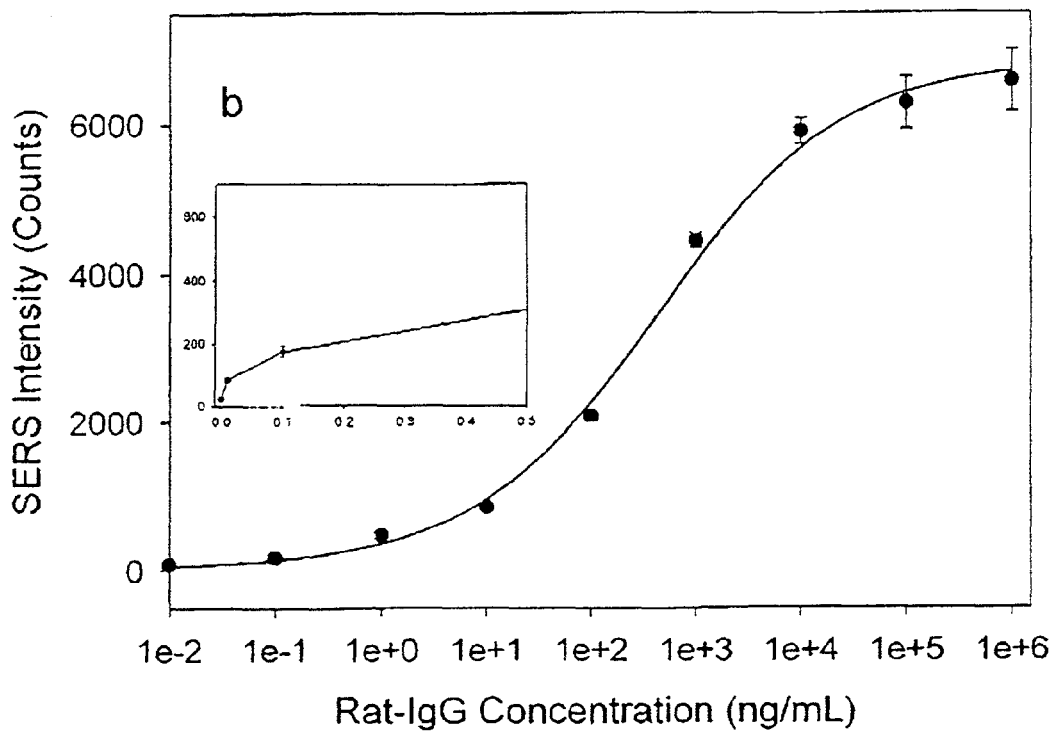

The strongest SERS band at 1075 cm$^{-1}$ was used as readout in the immunoassay experiments. FIG. 6 plots the intensity of this band versus the concentration of the antigen, rat IgG, with either the co-immobilized (6a) or the covalently-linked colloids (6b) as detection reagent. In both experiments, SERS signals show proportional response to the antigen concentration almost over the entire tested concentration range, representing a dynamic range of nearly 8 orders of magnitude. The solid lines represent the curve fitting of the immunoassay data based the four-parameter logistic model, a common regression model used for describing sandwich type immunoassays. The slope of the curve suggests how the readout signals quantify samples of different concentration; the larger the slope, the easier the distinction. Two important parameters obtained from the curve fitting will be discussed with more details in the later sections. One is the expected signal at zero dose, which is also called the negative control signal, the other is the expected signal at infinitely high or saturation dose, which is also called the positive control signal.

When working with samples at low concentration, we found it was more difficult to distinguish the analyte signal (S) accurately from that at zero dose than from the spectral noise (N). For example, even the signals from the negative control samples, were readily distinguishable from the noise in the spectra with S/N larger than 3 in both experiments. We therefore defined the limit of detection (LOD) as the concentration associated with a response three times the mean response obtained at zero dose. The LOD was around 0.2 ng/mL when employing the co-immobilized reagent, but lowered to 0.04 ng/mL with the use of the covalently-linked reagent.

The difference in LOD was largely due to the different SERS intensities observed for the two negative control samples, which were obtained through the same assay procedure, using samples at a concentration of zero (i.e., buffer only). Indeed, the difference in the negative control signals, which reflect different extents of nonspecific binding, is a major difference between the two sets of results. The colloidal reagent prepared using the co-immobilization approach seemed to yield a more pronounced nonspecific binding, and therefore, a higher Raman signal (145 counts) for the negative control sample (from curve fitting, S is 164 counts at zero concentration). In comparison, the colloids modified via the covalent linking approach yielded a much lower signal (22 counts) from the negative control (32 counts based on curve fitting). Because of the lack of a fluorescence background and lack of photobeaching of the Raman-active reagent, LOD values could be lowered by increasing the signal integration times.

Scanning Electron Microscopy images of these sample surfaces showed that a higher colloid density was observed on the capture antibody substrate when using the co-immobilized reagent, supporting the conclusion that a higher extent of nonspecific binding occurs with these samples. The increased nonspecific binding of the co-immobilized colloids was attributed to the weak interaction between the antibody and the colloid surface. This interaction is weakened due to the partial coverage of the reporter molecules on the colloid surface, which reduces the surface area on a colloid that can interact with the antibody and hence weakens the binding. This weak interaction can result in vacancies on the reporter-labeled immunogold colloid, and lead to its nonspecific binding with the antibodies on the capture substrate. Covalent coupling reduces this complication, which in turn, lowers the amount of nonspecific binding.

In addition to the negative control signal, all the spectra obtained with the covalently-linked colloidal reagent were of lower intensity than those obtained with the co-immobilized colloid for samples of same concentration. Based on the characterizations on the gold island film in FIG. 5, it is not believed that the lower intensity observed with the covalently-linked immunogold is due to the difference in the Raman scattering intensity between the DSB and DBA molecules. It is suspected that the lower signal in FIG. 6(*b*) may arise from an increased extent of antibody denaturation due to covalent linking, which lowers the "active" detection antibody levels on the colloid surface.

It is important to note that, although the co-immobilized colloids yielded much higher absolute Raman signals, the relative signals that normalized to the signal at zero dosage were always higher when using the covalently-linked reagent for detection. The curve fitting results show, for example, that the expected signal at the saturation dosage for the co-immobilized reagent is almost 2.5 times higher than that obtained using the covalently-linked reagent. However, the ratio for the signals at saturation dosage with respect to those at zero dosage is 50% larger for the covalently-linked reagent. The higher ratio suggests a sharper contrast between the positive and the negative control signal and therefore a more accurate distinction between an analyte and a blank sample.

The colloidal suspension prepared from the covalent linking approach was also more stable in solution and less susceptible to aggregation. These observations explain the lower run-to-run variation observed when using the covalently-linked reagent (~10%) compared to that when using the co-immobilized reagent (>20%). It was also noted that when starting with a new batch of reporter-labeled immunogold reagent, the batch-to-batch variation was even more significant and sometimes up to 100% when using the co-immobilized reagent. It is suspected that this difference represents the importance of the first step in the colloid modification. It is less critical in the covalent linking approach because DSB was always added at a level to ensure the exhaustive coverage of the reporters on every colloid. However, it is very critical in the co-immobilization approach since the dosage of DBA determined the reporter coverage on each colloid and hence the signal intensity per colloid.

We claim:

1. A Raman-active reagent comprising a Raman-active reporter molecule, a binding molecule, and a surface enhancing particle capable of causing surface enhanced Raman scattering, wherein said Raman-active reporter molecule is a non-polymeric monolayer and is covalently linked to the surface enhancing particle and provides a detectable or measurable Raman scattering signal when illuminated by an excitation source capable of inducing a Raman scattering, wherein the binding molecule is covalently linked to the Raman-active reporter molecule and is capable of specifically binding to a target analyte, and wherein the Raman-active reporter molecule operably links the binding molecule to the surface enhancing particle to form a Raman-active reagent.

2. The Raman-active reagent of claim 1 wherein the binding molecule is selected from the group of lectins, lectin fragments, lectin derivatives, antigens, monoclonal antibodies, polyclonal antibodies, immunoreactive fragments, immunoreactive derivatives, peptides, haptens, aptamers, nucleic acid molecules, crown ethers, cyclodextrins, cryptands, and calixarenes.

3. The Raman-active reagent of claim 1 wherein the Raman-active reporter molecule is selected from the group consisting of dithiobisbenzonic acid, 4-mercaptobenzoic acid, 2-naphthalenethiol, thiophenol, 4,4'-dithiobis(succinimidylbenzoate), direct red 81, Chicago sky blue, p-dimethylaminoazobenzene, 4-(4-Aminophenylazo)phenylarsonic acid monosodium salt, 1,5-difluoro-2,4-dinitrobenzene, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

4. The Raman-Active reagent of claim 1 wherein the surface enhancing particle comprises a metallic material.

5. The Raman-active reagent of claim 4 wherein the metallic material is either gold, silver, copper, platinum, aluminum, gallium, indium, zinc, cadmium, lithium or sodium.

6. The Raman-active reagent of claim 5 wherein the metallic material is gold.

7. The Raman-active reagent of claim 1 wherein the surface enhancing particle is either a silica, plastic, glass, carbon, ceramic or magnetic material, coated with a metallic material.

8. The Raman-active reagent of claim 7 wherein the metallic material is either gold, silver, copper, platinum, aluminum, gallium, indium, zinc, cadmium, lithium or sodium.

9. The Raman-active reagent of claim 8 wherein the metallic material is gold.

10. The Raman-active reagent of claim 1 wherein the binding molecule is operably linked to the Raman-active reporter molecule by a linker molecule.

11. The Raman-active reagent of claim 1 wherein the Raman-active reporter molecule is operably linked to the surface enhancing particle by a linker molecule.

12. A kit for determining the presence or amount of a target analyte in a test sample, the kit comprising:
    (a) a Raman-active reagent comprising a Raman-active reporter molecule, a binding molecule, and a surface enhancing particle capable of causing surface enhanced Raman scattering, wherein said Raman-active reporter molecule is a non-polymeric monolayer and is covalently linked to the surface enhancing particle and provides a detectable or measurable Raman scattering signal when illuminated by an excitation source capable of inducing a Raman scattering, wherein the Raman-active reporter molecule operably links the binding molecule, capable of specifically binding to a target analyte, to the surface enhancing particle, to form a reagent/analyte complex; and
    (b) a substrate capable of binding the target analyte or the reagent/analyte complex prior to inducing Raman scattering with the excitation source.

13. The kit of claim 12 wherein the binding molecule is selected from the group of lectins, lectin fragments, lectin derivatives, antigens, monoclonal antibodies, polyclonal antibodies, immunoreactive fragments, immunoreactive derivatives, peptides, haptens, aptamers, nucleic acid molecules, crown ethers, cyclodextrins, cryptands, and calixarenes.

14. The kit of claim 12 wherein the Raman-active reporter molecule is selected from the group consisting of dithiobisbenzonic acid, 4-mercaptobenzoic acid, 2-naphthalenethiol, thiophenol, 4,4'-dithiobis(succinimidylbenzoate), direct red 81, Chicago sky blue, p-dimethylaminoazobenzene, 4-(4-Aminophenylazo)phenylarsonic acid monosodium salt, 1,5-difluoro-2,4-dinitrobenzene, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

15. The kit of claim 12 wherein the surface enhancing particle comprises a metallic material.

16. The kit of claim 15 wherein the metallic material is either gold, silver, copper, platinum, aluminum, gallium, indium, zinc, cadmium, lithium or sodium.

17. The kit of claim 16 wherein the metallic material is gold.

18. The kit of claim 12 wherein the surface enhancing particle is either a silica, plastic, glass, carbon, ceramic or magnetic material, coated with a metallic material.

19. The kit of claim 18 wherein the metallic material is either gold, silver, copper, platinum, aluminum, gallium, indium, zinc, cadmium, lithium or sodium.

20. The kit of claim 19 wherein the metallic material is gold.

21. The kit of claim 12 further comprising a nonspecific binding ingredient or a stabilizing ingredient.

* * * * *